US 8,068,051 B1
Nov. 29, 2011

(12) United States Patent
Osterweil

(10) Patent No.: US 8,068,051 B1
(45) Date of Patent: Nov. 29, 2011

(54) METHOD AND APPARATUS FOR A BODY POSITION MONITOR USING RADAR

(76) Inventor: Josef Osterweil, Rockville, MD (US)

(*) Notice: Subject to any disclaimer, the term of this patent is extended or adjusted under 35 U.S.C. 154(b) by 0 days.

(21) Appl. No.: 12/931,278

(22) Filed: Jan. 28, 2011

Related U.S. Application Data

(63) Continuation of application No. 12/456,328, filed on Jun. 16, 2009, now Pat. No. 7,916,066, which is a continuation-in-part of application No. 11/789,512, filed on Apr. 24, 2007, now Pat. No. 7,377,177.

(51) Int. Cl.
*G01S 13/00* (2006.01)
*G08B 23/00* (2006.01)

(52) U.S. Cl. ...... 342/28; 342/27; 340/573.1; 340/573.4; 340/573.5; 340/573.7; 340/575

(58) Field of Classification Search ............... 342/22, 342/27, 28; 340/573.1, 573.4, 573.5, 573.7, 340/575; 382/115
See application file for complete search history.

(56) References Cited

U.S. PATENT DOCUMENTS

| | | | | | |
|---|---|---|---|---|---|
| 3,796,208 | A | * | 3/1974 | Bloice | 600/534 |
| 4,981,139 | A | * | 1/1991 | Pfohl | 600/484 |
| 5,573,012 | A | * | 11/1996 | McEwan | 600/595 |
| 5,766,208 | A | * | 6/1998 | McEwan | 600/595 |
| 5,825,293 | A | * | 10/1998 | Ahmed et al. | 340/573.1 |
| 5,905,436 | A | * | 5/1999 | Dwight et al. | 340/573.1 |
| 6,049,281 | A | * | 4/2000 | Osterweil | 340/573.4 |
| 6,160,478 | A | * | 12/2000 | Jacobsen et al. | 340/539.12 |
| 6,201,476 | B1 | * | 3/2001 | Depeursinge et al. | 340/573.1 |
| 6,225,906 | B1 | * | 5/2001 | Shore | 340/573.4 |
| 6,333,694 | B2 | * | 12/2001 | Pierce et al. | 340/573.1 |
| 6,466,125 | B1 | * | 10/2002 | Richards et al. | 340/573.4 |
| 6,611,206 | B2 | * | 8/2003 | Eshelman et al. | 340/573.1 |
| 6,696,957 | B2 | * | 2/2004 | Shepher | 340/573.1 |
| 6,765,992 | B2 | * | 7/2004 | Dawson | 379/38 |
| 7,001,334 | B2 | * | 2/2006 | Reed et al. | 600/300 |
| 7,106,885 | B2 | * | 9/2006 | Osterweil et al. | 382/103 |
| 7,242,305 | B2 | * | 7/2007 | Cuddihy et al. | 340/573.1 |
| 7,272,431 | B2 | * | 9/2007 | McGrath | 600/509 |
| 7,345,618 | B1 | * | 3/2008 | Cole et al. | 342/22 |
| 7,567,200 | B1 | * | 7/2009 | Osterweil | 342/28 |
| 7,646,307 | B2 | * | 1/2010 | Plocher et al. | 340/573.1 |
| 7,656,299 | B2 | * | 2/2010 | Gentry et al. | 340/573.1 |
| 7,893,844 | B2 | * | 2/2011 | Gottlieb | 340/573.1 |
| 7,905,832 | B1 | * | 3/2011 | Lau et al. | 600/300 |
| 7,916,066 | B1 | * | 3/2011 | Osterweil | 342/28 |
| 2002/0158790 | A1 | * | 10/2002 | Fullerton et al. | 342/28 |
| 2004/0027270 | A1 | * | 2/2004 | Fullerton et al. | 342/28 |
| 2008/0074307 | A1 | * | 3/2008 | Boric-Lubecke et al. | 342/28 |

OTHER PUBLICATIONS

T. Hori, Y. Nishida, "Ultrasonic Sensors for the Elderly and Caregivers in a Nursing Home," Proceedings of the 7th International Conference on Enterprise Information Systems ICEIS 2005, Vo. 5, pp. 110-115, May 2005.*

* cited by examiner

*Primary Examiner* — Thomas Tarcza
*Assistant Examiner* — Peter Bythrow

(57) ABSTRACT

A radar system for monitoring a premises in a home or building. The radar system includes transmitter and receiver antennae and a signal processor that processes a reflected signal. Doppler analysis of the reflected signal determines the activity and location of a subject's upper torso, and the subject's presence within the monitored premises.

14 Claims, 11 Drawing Sheets

METHOD AND APPARATUS FOR A BODY POSITION MONITOR USING RADAR

RELATED DATA

The present application is a Continuation of U.S. application Ser. No. 12/456,328 entitled "METHOD AND APPARATUS FOR A BODY POSITION MONITOR AND FALL DETECTOR USING RADAR" which was filed on Jun. 16, 2009, and is a Continuation-In-Part of U.S. application Ser. No. 11/789,512 entitled "METHOD AND APPARATUS FOR A BODY POSITION MONITOR AND FALL DETECTOR USING RADAR" which was filed on Apr. 24, 2007, both applications commonly assigned and incorporated herein by reference. The present application also expressly incorporates by reference herein the entire disclosure of U.S. Provisional Applications Nos. 60/795,277, entitled "Method and apparatus for a three-dimensional positioning system using Ultra-Wideband radar", which was filed on Apr. 27, 2006; 60/831,063, entitled "Method and apparatus for a body position monitor and fall detector using Ultra-Wideband radar" which was filed on Jul. 17, 2006; and 61/130,300 "METHOD AND APPARATUS FOR A BODY POSITION MONITOR AND FALL DETECTOR USING RADAR" which was filed on May 30, 2008.

FIELD OF THE INVENTION

The present invention is directed to an apparatus and method for automatically identifying a subject, such as, for example, a human or animal, who has fallen while in a defined three-dimensional (3-D) space, determining the physical position of the subject, and evaluating the position with respect to particular assessment criteria. More specifically, the present invention relates to the use of radar including generation and subsequent analysis radar return signals to determine whether the data correlates to a condition requiring immediate attention. In this discourse, the term radar is used in the broadest sense and consists of signal emission and reflected signal reception from a target in its path. This definition includes a variety of spectral regions and media including, but not limited to, electromagnetic (such as radio wave or light (laser) radar) and acoustic media echo radar. The examples of radar medium and technology described herein shall not limit the scope of the claims appended hereto. It is recognized that specific choices of medium and spectrum may exhibit specific and diverse performance attributes. Note that micro-power impulse radar (MIR) and ultra wideband (UWB) radar are used interchangeably throughout this discourse, and represent the generic wideband radar family.

BACKGROUND AND RELATED INFORMATION

The present invention has broad application in situations including, but not limited to, the following topics.

People who are elderly, infirm, chronically ill, confused, or are otherwise unable to care for themselves and very often fall with resulting medical distress, often reside in a nursing home or similar type institution. Similarly, others who find that living alone is unacceptably difficult or risky may elect to reside in an assisted living facility, or the like, that assists their residents in the performance of certain daily living tasks (such as, for example, bathing and dressing). Both such institutional facilities—nursing homes and assisted living facilities (and the like)—monitor their residents' health and safety, and respond to requests for emergency assistance. In a typical assisted living or nursing home, a limited number of staff members are available to monitor a relatively large number of residents (or patients).

Alternatively, such care and monitoring services are generally available for those who wish to reside in a home setting, and require assistance with, for example, toileting, cooking, cleaning and performing routine house chores or. In a home setting, one or more attendants provide care and monitoring for, typically, one or two residents.

In the settings described above, there may be an urgent need by one of the residents for a rapid response as a result of a fall. Often, that need arises when the resident falls, for example, while trying to get out of bed. In such a situation, the required rapid response might not be timely, due to the unavailability of an attendant. In such a case, the resident would have to remain lying on the floor until the aide returns. In the absence of the required rapid response, serious injury, or even death, may occur.

This risk is compounded when an attendant is not witness to, or present during, the urgent event. Attendants may be unavailable for several reasons, including, but not limited to: attendants are busy tending to other patients; attendants are performing part of their service at a remote location (shopping, for example); or the resident's contracted level or privacy precludes continuous personal attention.

Additionally, people who are able to care for themselves in their homes, but wish to mitigate the risks associated with falls, such as being helpless and/or injured as the result of the fall, employ automatic monitoring and emergency call services.

According to the New England Journal of medicine, over 10M Americans over 65 live alone. Of these, over 25% (2.5M) of these subjects fall once per year, and for 50% of these falls, the subject can't get up. Studies further show that 38% of survivors found helpless do not return to independent living. For those subjects that are down without assistance for greater than 72 hours, the mortality rate is 67%. For those that are down less 1 one hour without assistance, the mortality rate is 12%. Thus, there is a substantial need for solutions that mitigate falls, especially for persons living alone at home. Currently available solutions have not fulfilled this need.

Note that phrases, such as, but not limited to, care-givers, staff, staff member, monitoring personnel, attendant, attending personnel, etc., refer to a person located on or off the premises (facility or home) where the individual (subject) is being monitored, and may include, for example, an emergency call service or a neighbor of the monitored individual.

While falling (from a bed, standing position, etc.) is a major cause of injury for patients, the present invention applies directly to any other situation for potentially dangerous or risky changes in elevation.

Generally, animals (such as dogs or horses) may be the subject of care and monitoring, similar to the situation described above for people.

More specifically, animals, such as horses, often represent a significant investment that owners wish to preserve. Some animals, such as horses, maintain a predictable posture (for example, standing), such that a deviation from that posture may be regarded as abnormal and requiring immediate attention. Such a situation may exist when the animal is either in good health or is infirm.

For both home and the institutional settings, apparatus are available to summon (call) aid. Such call systems employ both active and passive invocation methods, where an active method requires activation (typically conscious) by the patient, and passive means that the system automatically makes the call, in response to some automatic invocation. An example of call system is the "call bell" used in hospitals.

The majority of currently available solutions require the subject to wear some kind of device. An additional problem associated with such devices is what can be termed the "pride factor". Many people find that the requirement to wear a visible device essentially marks them as a person who is challenged, and as a result there are many instances of people who have fallen and been on the floor for extended periods because they "forgot" to wear the device. A passive solution which does not require the user to wear any form of device has a significant advantage in this regard.

The purposeful combination and integration of monitoring system and call system satisfies the need of the caregiver to detect and report potentially dangerous situations such as falls.

SUMMARY OF THE INVENTION

The present invention is a uni-dimensional application of radar such as but not limited to UWB radar with the goal of remotely and automatically detecting, the three-dimensional (3D) position of a human or animal subject (with emphasis of position relative to the floor), in a manner that overcomes the challenges presented by physical obstructions (such as furniture), and without requiring activation by the subject or involving an apparatus located on the subject.

The present invention is a uni-dimensional application of radar such as but not limited to UWB radar with the goal of remotely and automatically detecting the two-dimensional (2D) position of a human or animal subject relative to the floor, in a manner that overcomes the challenges presented by physical obstructions (such as furniture), and without requiring activation by the subject or involving an apparatus located on the subject. The 2D detection disposes with azimuth information for fall detection.

An application of the invention relates to an automated system that identifies when a subject is in a position that requires immediate attention, especially when physical obstructions might otherwise impair visual detection, with primary focus on fall detection.

Accordingly, the present invention provides an ancillary, passive call capability, which one skilled in the art may interface with a commercial call system. This is particularly important where, for example, the monitored individual loses consciousness; a fall renders an active calling device unreachable; the individual (such as, for example, an Alzheimer's patient) is confused; the subject has low vision and thus is unable to find the signaling device; the signaling device has low battery; the subject is not proximate the signaling device; or in any case where false alarms may otherwise be expected.

The primary benefit of the present invention is the ability to achieve these goals using a radar application, which has the appropriate characteristics. Accordingly, the invention employs a common wide-beam antenna, which is more cost effective and suitable for wideband application than is a scanning narrow-beam antenna.

According to an object of the present invention, a method is disclosed for detecting and analyzing the position of a subject. Radar generated signals, such as but not limited to UWB or FMCW (Frequency Modulated Continuous Wave—usually triangular modulating signal) radar generated signals of at least one of a single frequency; a modulated carrier frequency; a series of single impulses; a series of time encoded impulses; and spread spectrum bursts for a monitored area that includes a subject to be monitored, is captured by, for example, a computer for analysis. The analysis determines the presence of a subject, specifically the subject's upper torso, its location, and its elevation above the floor level. An undesired proximity of the subject's upper torso to the floor is indicated, by, for example, an alarm. The alarm may be interfaced to, for example, an existing alert system.

According to yet another object of the present invention a method is disclosed for detecting and analyzing the changes in the position of a subject and/or the rate of the change. As the radar data is collected for analysis of the presence and location of a subject's upper torso's internal and rhythmic motion, the data is also analyzed for subject's external body motion which is outside the spectrum of the subject's upper torso activity. This additional analysis result provides further clues as to whether a fall has occurred.

According to a feature of the present invention, the radar data is analyzed concurrently for independent specific attributes, such, as but not limited to, heartbeat, respiration, body motion, and body motion velocity. By applying fine-tuned signal processing analyses selective for each attribute independently, the evaluation of these attributes yields enhanced fall determination reliability.

According to a feature of the present invention, the radar data is Doppler analyzed concurrently for additional independent specific attributes, such as, vibrating tags that vibrate at different frequencies may each be used as a marker for the radar, such as, but not limited to, a caregiver presence detection, a calibration device, delimiter of specific physical boundary, etc.

According to a feature of the present invention, radar units are distributed throughout the monitored area detect the presence of a subject by signal processing, including Doppler analysis such as filtering, limiting the frequencies of interest to the lung and/or heart movement rates.

According to yet another feature of the invention, radar units detect the presence of a subject by analysis of random movements of the subject and the intensity of said random movements as a continuous function of their distance from the floor.

According to another feature of the invention, radar units detect the presence of a subject by analysis of random movements of the subject that fall within the spectrum of human activity. The analysis derives a distribution of their intensity as a continuous function of their distance from the floor.

According to yet another feature of the present invention, radar units detect the presence and location of a subject by analysis of random movements of the subject and their intensity as a continuous function of their distance from the antennae cluster and azimuth.

According to yet another feature of the present invention, radar units detect the presence and location of a subject by analysis of random movements of the subject and their intensity as a continuous function of their distance from the antennae cluster and azimuth in addition to the distribution of their intensity as a continuous function of their distance from the floor.

According to another feature of the invention, an analyzed radar signal is restricted by at least one of a time gate that places the signal at a predetermined distance range from the radar unit and a triangulation based on round trip time of at least two radar receivers.

According to another feature of the invention, the Doppler data is compiled in a low frequency spectrum compared to the sampling rate (pulse repetition rate) used by the radar. Therefore, spatially diverse antennae may be multiplexed into a single receiver without compromising the compiled Doppler data derived from each antenna. For example, every other return signal at each antenna is processed by the receiver in the case of two receive antennae. The compiled Doppler data of each input is stored separately for subsequent correlation, triangulation, etc. Note that the transmitter multiplexing to two or more antennae with a single receiver antenna, accomplishes the same task of triangulation. Therefore, no further clarification is provided for the reciprocal nature of the transmit and receive function as it related to triangulation.

According to yet another feature of the invention, the transmitter impulse or FMCW output is modulated by data to be communicated to other radars within the receiving range to form a network for multi-radar housekeeping functions, such as, but not limited to, sharing status, configuration control, alarm condition conveyance, etc. This does not preclude the use of independent communications for a multi-radar system in addition or instead. This communication is not limited to a wireless physical layer.

According to another feature of the invention, time multiplexing of housekeeping communications and radar functions are assigned separate time slots.

According to another feature of the invention, a single radar pulse generator (transmitter) is strategically located with at least two radar receivers or one multiplexed receiver or conversely, a single receiver with at least two radar transmitters or single multiplexed transmitter that determine the position of a subject, for example, relative to the floor. Furthermore, two or more receivers or one multiplexed receiver and their respective pulse roundtrip delays provide data for determining subject's 2D or 3D spatial position. Initial calibration further enhances this capability. Location of transmitters and receivers in present invention are represented by the location of their respective antennae.

According to another feature of the invention, signal processing is employed for radar signal analyses including sequential return signal integration, Fast Fourier Transform (FFT), and signal correlation.

A still further feature of the present invention is the ability of tracking an individual by perturbation to the originally transmitted signal, such as, the Doppler Effect and corresponding analysis of the subject's upper torso for heart and/or lung movements while the heart rate and/or breathing rate vary in accordance with the subject's activity. This is accomplished by the use of wider band filters which introduce a degradation of signal to noise ratio and/or by adaptive signal processing (ASP), a technique suitable for the filter sliding along the frequency scale as the signal's rate changes. ASP is particularly suitable for tracking a subject because the heart or lung rates generally change gradually rather than in sudden steps. Individual tracking and monitoring a subject's location allows data collection on an individual's general behavioral patterns. Tracing behavior that is out of character can provide an indication that help may be necessary.

According to another object of the present invention, an apparatus for monitoring a position of a subject is disclosed, comprising of at least one of a radar with a steerable directional receive antenna and distributed radars with fixed beam receive antennae, a processing device that processes the captured radar signals where the processing device produces a direction and distance (akin to polar coordinates) of the upper torso of a subject and determines whether a fall has occurred by the proximity of subject's upper torso to the floor, and a notification device that provides a notification when the processing device determines that the subject is substantially horizontal. The notification device and the processing device may be located in different locations.

According to a still further advantage of the invention, by default the analyzed radar signal provides heart rate and lung function (respiration rate) for further analyses of irregularity, a condition that is then reported similarly to a fall alarm.

According to a further advantage of the invention, the analysis of the signals of the radar clusters filter out and disregard signals that are not related to subjects activity, such as but not limited to, vibration of appliances and other signals outside the range of the human activity spectrum.

According to another object of the invention, a method is disclosed for monitoring a position of a subject in a predetermined volume. Each radar or cluster operates autonomously in monitoring a subject (cluster is discussed further later). When the coverage area exceeds the capacity of one radar cluster more radar clusters are used. Handover of monitoring from one radar cluster to another is determined by the physical location of the monitored subject and signal strength related to the beating heart and/or lung movements at one radar cluster compared to an adjacent radar cluster where the beating heart and/or lung movement signals are dominant. Optionally, this roaming handover is coordinated in a systematic manner similar to cell phone roaming techniques.

The radar cluster performance is further enhanced by post installation calibration. Such calibration provides correction data for strategic points of the monitored premises such as, but not limited to, room corners at floor level, center of the room at floor level, doorways, etc. Virtual mapping of the premises obtained from such calibration attains better system accuracy and enhances system's tracking capability of a subject.

Another advantage of the invention includes a static signature of the reflected signal stored as reference for each radar cluster. A change in signature could be an indication that a subject may have entered the monitored space for the given radar cluster and therefore a search for the upper torso is launched. If none is found, the radar cluster assumes a standby state and stores the new signature as the reference. A standby mode of a radar cluster in a multiple radar cluster system saves on network resources and processing power of the system. The network architecture used for this communication could be either a wireless mesh network or alternately a point-to-multipoint network architecture.

According to an advantage of the invention, clusters comprising one transmitter and multiple receivers are deployed in a space diverse fashion for enabling triangulation of a desired reflecting object. In the present invention, space diversity refers to the respective antennae locations. Where the radar data collection rate is high relative the movement of the subject being monitored, a single receiver can be timeshared between several spatially diverse receive antennae. The same holds true for one transmitter with multiple transmit antennae.

According to an advantage of the invention, multiple hearts beating and/or lung movements at a radar unit is an indication of at least one additional collocated individual. However, if one or more individuals are present, the process of monitoring heart beat and/or lung movement as well as the heart/lungs' distance from the antenna, determines the condition at the scene. Correlation of return signal segments relating to the heart/lungs determines those emanating from each individual for unambiguous processing of the location of each individual's upper torso.

According to another feature of the invention, a status of the subject whose heart beat and/or lung movement ceases is optionally interpreted as an alert condition by the system unless the roaming trace indicates that the subject left the premises.

According to a feature of the invention, the apparatus further comprises an optional audio capture device that captures sounds associated with the subject. The processing device analyzes the emitted sounds to derive cues pertaining to a position of the subject. The cues are derived from voice recognition of the emitted sounds and/or a voice stress analysis of the emitted sounds. It is noted that cues from other sources, such as for example, video camera signal, infrared, and radio signals are within the scope of this invention as supplementary information sources for determining an individual's distress.

According to another feature of the invention, the apparatus further comprises an audio messaging device that announces that a fall has been detected. The subject has a predetermined amount of time to cancel the alert condition in case of a false alarm. If the alarm is not canceled within the appropriate time period, the alarm is conveyed to a caregiver authority. This feature is particularly important when the subject lives alone and where the caregiver is not located on the premises.

According to an advantage of the invention, a voice communication between the subject and the caregiver authority is established by the caregiver to further determine the severity of the alert condition. This feature is particularly important when the subject lives alone and where the caregiver is not located on the premises.

Another advantage of the invention includes a visual display device that provides a visual image of the subject when the notification device provides the notification that the subject is substantially horizontal. The visual display device and/or the notification device provides optional supplemental information related to the subject.

The apparatus may be integrated into any call system, and is compatible with call system protocols. Accordingly, it may be controlled and reset locally or remotely.

An advantage of current invention is that the 2D detection disposes with azimuth information for fall detection and utilizes a vertical cluster of at least one transmitter and two receiver antennae. This cluster enables easy installation, for example, vertically against the wall at floor level. In conjunction with wireless communications, for example, the connectivity for installation requires only access to a power outlet.

An advantage of the current invention is the optional integration of the radar fall detector with a prior art Personal Emergency Response System (PERS) for the purpose of providing the subject with a means to summon help at will whether or not a fall has occurred. Such as but not limited to, onset of dizziness, severe nausea, etc. This option does require the subject to wear a manually activating device, such as a button, with a transmitter or reach for activation devices placed strategically on the premises.

Another advantage of the current invention is that unlike motion sensors that monitor daily activities of a subject by the general location that the activity occurred, and at a given time of the day, this invention actually tracks the subject even while immobile.

BRIEF DESCRIPTION OF THE DRAWINGS

The foregoing and other objects, features and advantages of the invention will be apparent from the following description of preferred embodiments, as illustrated in the accompanying drawings which are presented as a non-limiting example, in which reference characters refer to the same parts throughout the various views, and wherein.

DETAILED DESCRIPTION OF THE INVENTION

The particulars shown herein are by way of example and for purposes of illustrative discussion of embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description taken with the drawings making apparent to those skilled in the art how the present invention may be embodied in practice.

Figure 6:
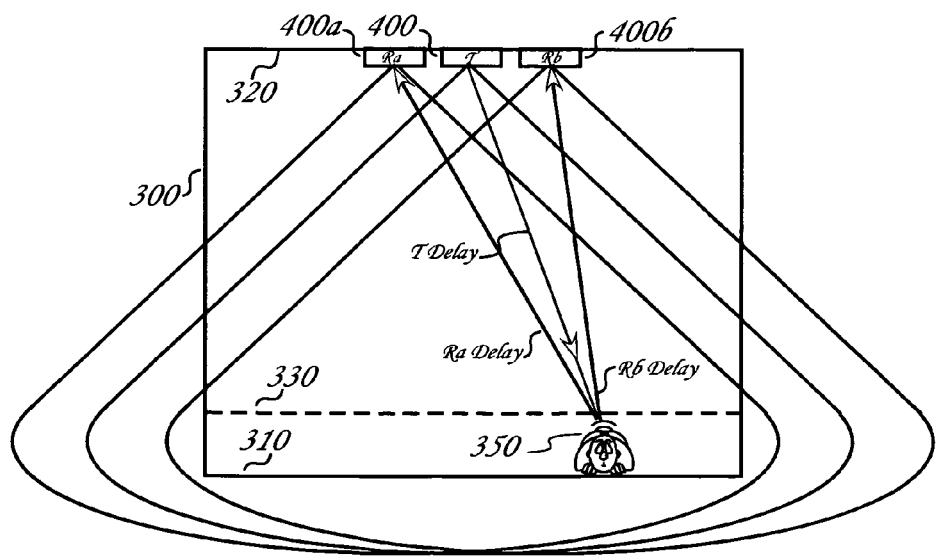
FIG. 6 illustrates a radar cluster concept of one transmitter and two receivers.
Figure 11:
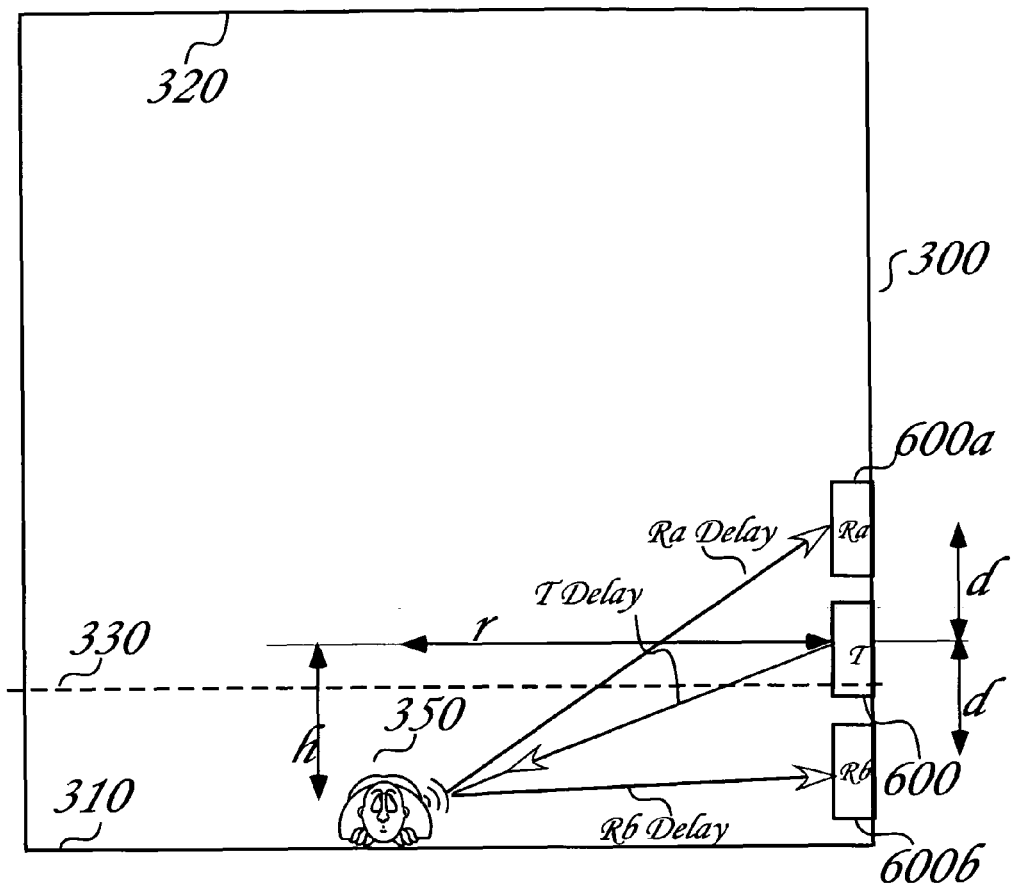
FIG. 11 illustrates an example of a cross-section of a room where a vertical 2D cluster detects a fallen subject.

The present invention is a fall detector based on a quantitative spatial analysis of a subject 350 in a monitored volume (i.e., in close proximity, such as, for example, a room 300 and/or corridor—see FIG. 6 and FIG. 11) and the processing of the captured image to determine physical characteristics and other features of a monitored individual. In this regard, while the present invention will be described with respect to the monitoring of a single subject (such as, for example, an individual), it is understood that the instant invention is equally applicable to monitoring a plurality of subjects (which may be, for example, individuals and/or animals).

UWB Radar includes a single impulse transmission at a repetition rate optimized to the radar range and return signal processing time, an impulse burst sequence coded in accordance with a high autocorrelation pattern, and spread spectrum. Obtaining a precise signal roundtrip time can be further enhanced through the use of correlation process as known to those skilled in the art. Doppler radar requires integration of multiple signal returns and focusing differential patterns of the signal.

The application of Doppler UWB radar processing has particular appeal for differentiating the monitored subject, such as a living person, from inanimate objects contained in the monitored volume of interest. The Doppler signals of interest are reflections of the upper torso linked to the beating heart and the motion of breathing lungs, vertical movement toward the floor by the subject, as well as body movement in general. This approach monitors the subject when in static position as long as the heartbeat and/or lung motion can be detected. Contrarily, other body motions, toward the floor in particular, are transient. The consequence of static phenomena for use as primary fall detection criteria is the ability to confirm and reconfirm that a fall has occurred long after the transient phenomena have dissipated. For example, when a fall occurs in a segment of time where a transient phenomena monitoring system did not report a fall due to, such as, a sensor's misinterpretation, momentary noise on communications channel or power outage, etc., the fall will not be subsequently detected. This distinguishes the static phenomena monitors of present invention, from most other fall detectors of prior art. The heart and the lungs have a rhythmic motion and are therefore better suited for Doppler detection by limiting the signal detector to a narrower band in a predetermined spectrum range. The radar signal processing of the heartbeat alone or of the lung movement alone provides even more selective detection (narrower band) for each relative to the bandwidth required for both. Furthermore, the body motion toward the floor as an indicator of the rate of fall and is likely to be in a different band segment and bandwidth than the heartbeat or the lung movement. Processing the same radar data for the three different attributes, according to the above example, can be executed concurrently and render a fall/no-fall detection rapidly and with high probability for accuracy. Moreover, adaptive signal processing adjusts the filter's spectral response to changes of heart beat rate and/or breathing rate resulting from various activities of the subject. Digital processing techniques that learn the recurring behavior patterns for optimizing detection are apparent to those skilled in the art. Furthermore, radar's receiver time gating limits signals for subsequent processing that are reflected from distance ranges commensurate with the segment of the monitored volume where a beating heart or breathing lungs can be found. For example, there is no point monitoring above 5 feet from the floor which includes tracking of individual's presence, or above the fall defined threshold if individual tracking is not desired. This restriction eliminates dealing with unproductive processing of noise interference.

As employed in the following discussion, the term "volume" represents a three-dimensional region, such as, for example, the interior of a room. Any location within the volume can be uniquely identified by a coordinate system. Each location in the volume is "monitored" if at least one capture device (to be discussed below) has a view of the location.

In one embodiment, a cluster of one UWB transmitter and four UWB receivers as in FIG. 8, is employed to look for and capture all significant parts of the volume in which the subject resides that are to be monitored. UWB is penetrable through most common furniture (i.e., chairs, dressers, bookcases, etc.) and therefore these visual obstructions do not interfere with the sensor's viewing (monitoring). Note that the clusters discussed herein employ a single transmitter and multiple receivers. However, the present invention is not limited to this cluster configuration and includes other transmitter/receiver combinations not illustrated. For example, the use of a single receiver and single transmitter, single receiver and multiple transmitters, multiple receivers and single transmitter, and multiple transmitters and multiple receivers.

The data obtained from the UWB radar includes Doppler signals from the monitored volume and radar roundtrip delay time. The Doppler signals are effective for isolating moving objects from static clutter. Note that the term Doppler is herein used in the broader term as commonly used in the industry to refer to retrieving a signal based on the differences between successive radar returns rather then just frequency shift. The concept of frequency shift is not applicable in a UWB-based radar embodiment due to its wideband, multi-frequency nature. This distinction is emphasized because the goal of this radar is to ascertain a moving target's location and distinguish it from stationary clutter. The Doppler signal is further selectively filtered for flexibility in scrutinizing specific objects, such as, but not limited to, for example, a person's gait, a person's heart beat, and a person's lung function. The selective filtering of the radar data enables an optimized detection of each aspect of the subject's activity. For example, the radar data is first analyzed for heart beat in the specific heart rate spectrum (typically rhythmic phenomenon). The location of the upper torso proximate to the floor is a compelling criterion for fall detection. Optionally, the same radar data is also independently analyzed for lung activity spectrum, also rhythmic in nature, and/or for overall body movements (typically non rhythmic) as additional clues. The rate of the body's movement, for example, in a vertical downward direction can be considered as part of the criteria for fall detection. The roundtrip time delay determines the distance of a specific reflecting element to the cluster.

The preferred embodiment cluster is based on one transmitter and at least two space diverse receivers. References to the location of transmitters and receivers in the present invention indicate the physical location of the signal interface i.e. their respective antennae. In present invention, collocated transmit and receive antennae are equivalent to a shared a common antenna structure for both transmit and receive functions. In this context, the transmit antennae and the receive antennae refer to the functional attributes rather than physical entity. Cluster space diversity pinpoints the location of a reflecting object of interest. Three space diverse roundtrip time delay values provides enough data for a three dimensional location analysis relative to the cluster One skilled in the art will recognize that a number of alternatives, such as, for example, a UWB radar that moves on a rail (synthetic aperture radar), or panning, can be used to provide comparable data for three dimensional analyses. Spatial diversity of the transmit and receive antennae introduces timing measurement ambiguities that are mitigated by, but not limited to, carefully measured connecting cables between elements and calibration processes.

The UWB radar transmission consists of individual narrow sequential individual pulses; sequential pulse bursts coded with, such as, but not limited to, golden codes, and spread spectrum signal bursts. The precision of roundtrip time delay is typically obtained but not limited to correlation of the return signal to the transmitted signal. The cluster of the preferred embodiment is prefabricated for maintaining fixed cable length between cluster elements, thus the cable delays can be compensated for and the distance relevant delay can be determined with additional precision. However, it is understood that the approach is not limited to a particular cluster type or configuration. For example, a cluster that is prefabricated into a rigid frame, pre-wired, and ready for mounting on a ceiling, a wall, or a standalone version according to a template pattern, or other methods that will obtain (provide) required information for subsequent processing to determine subject's position in two-dimensions or three-dimensions. It is understood that a cluster can be mounted anywhere in addition to the ceiling and be within the scope and spirit of present invention.

UWB radar processing in conjunction with the distance of a valid Doppler signal from the radar as observed by the cluster determine the location of a beating heart and/or breathing lungs within the monitored volume of interest. Furthermore, as the individual leaves the monitored volume and roams into adjacent volume monitored by another radar cluster, such as adjacent rooms, the subject is tracked as to their whereabouts by the virtue of changes to the radar return signal. A UWB cluster is constantly processing the Doppler signal in a volume occupied by a subject; otherwise in the absence of a subject, the cluster records a static signal signature and periodically looks for changes in radar return signals (signatures). Various cluster power distribution, communication, network monitor and control techniques are available, such as, but not limited to, wired and/or wireless communications with multitude of protocols, and central and distributed network coordination. Each cluster in a given location is a part of a network which includes housekeeping coordination features. Such network coordination and communications techniques are apparent to those skilled in the art. However, each cluster in the preferred embodiment is autonomously monitoring its designated space. While, for example, the cluster(s) that are detecting the presence of a subject keep monitoring, for example, the position of the upper torso, the other clusters can optionally be in a standby mode. During the standby mode, the clusters periodically obtain the signature of the reflected signal and compare it to a previously recorded signature. If the new signature differs from the recorded one, an attempt to identify the presence of a subject is triggered. If a subject is present monitoring continues, otherwise the new signature is recorded for future reference and is stored in place of the previously recorded signature. Note that a signature can be comprised of a combination of a sequence of multiple reflections. The present invention is not limited by the above exampled scenario. The preferred embodiment's construction facilitates the antennae of the cluster to be oriented in a controlled manner. The antennae orientation determines the direction of the beam of each antenna so that they point in a coordinated direction i.e., at a common monitoring volume of interest. Additionally the antennae controlled orientation maintains appropriate antennae polarity for optimal radar performance. Further radar accuracy can be obtained by augmenting reflection time measurements with parasitic internal propagation time delays. These delays may change with age and variation in the environment, such as, but not limited to, temperature, humidity, pressure, etc. These parasitic propagation delays can be measured by, but not limited to, for example, loopback at different points in the cluster. Such procedures can be implemented as part of maintenance or as an automated self test at desired intervals.

Although the discussion has focused on the heart, lungs and vertical motion for high probability of accurate fall detection, the present invention is not limited to these three attributes. Monitoring other body motions, such as, but not limited to, gait pattern signatures, body gestures, and daily living patterns are possible and will further enhance fall detection, fall predictability, and subject wellbeing. The present invention, by storing signatures of body activity patterns, can relate to changes in those patterns and warn the emergency response center or caregiver that, for example, deterioration of subject's patterns has occurred and subject's reevaluation is called for. Monitoring of daily living patterns by subjects using a variety of sensors has been proven to be effective in deriving conclusions about the general wellbeing of the subject.

Furthermore, the UWB radar fall detector can be enhanced by the integration or augmentation of current art techniques for, for example, fall monitoring, personal emergency response system, etc.

Figure 1:
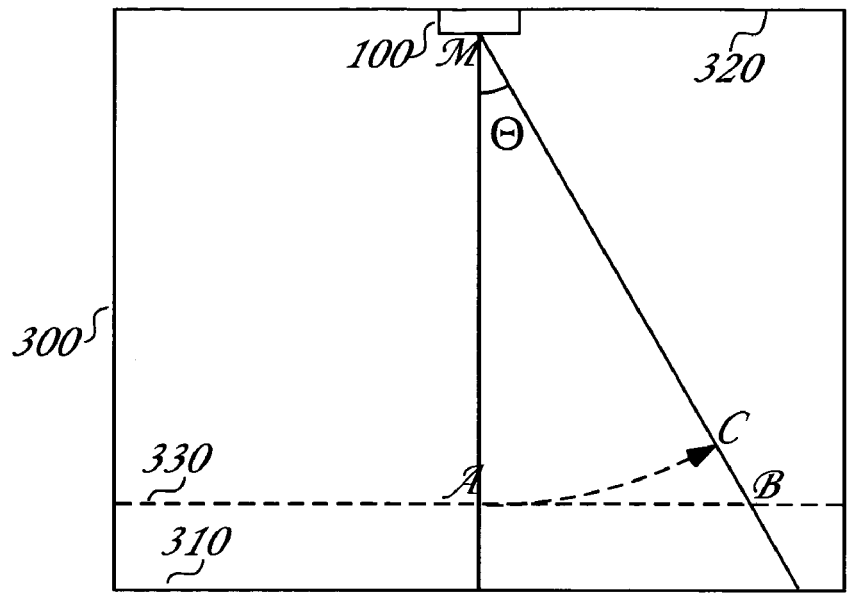
FIG. 1 illustrates an example of a the discrepancy in distance determination from the radar 100 and the floor 310 as a function of viewing angle.

Although the preferred embodiment is described as a cluster of spatially diverse radar elements, this invention is not limited to said configuration. A single radar element is equally applicable. For example, one approach necessitates a narrow beam radar antenna the can be directed for scanning of the monitored volume of interest. Alternately, a plurality of fixed position UWB radar elements distributed in a manner that encompasses the monitored volume of interest can provide the similar results. FIG. 1 illustrates an example of a sensor that is useable with the present invention. As shown in FIG. 1, a radar device 100 mounted on ceiling 320, such as, but not limited to, an UWB radar, is employed to capture a vertical distance from a floor 310 relative to a threshold 330 of a subject, such as, but not limited to, for example, an individual. In the embodiment of FIG. 1, the sensor 100 perceives the threshold 330 in terms of its distance to the subject as a function of a viewing angle $\Theta$. In this regard, while an azimuth viewing the threshold is at point A and the view at an angle $\Theta$ the threshold is at point B a resulting distance discrepancy is the segment BC.

Figure 2:
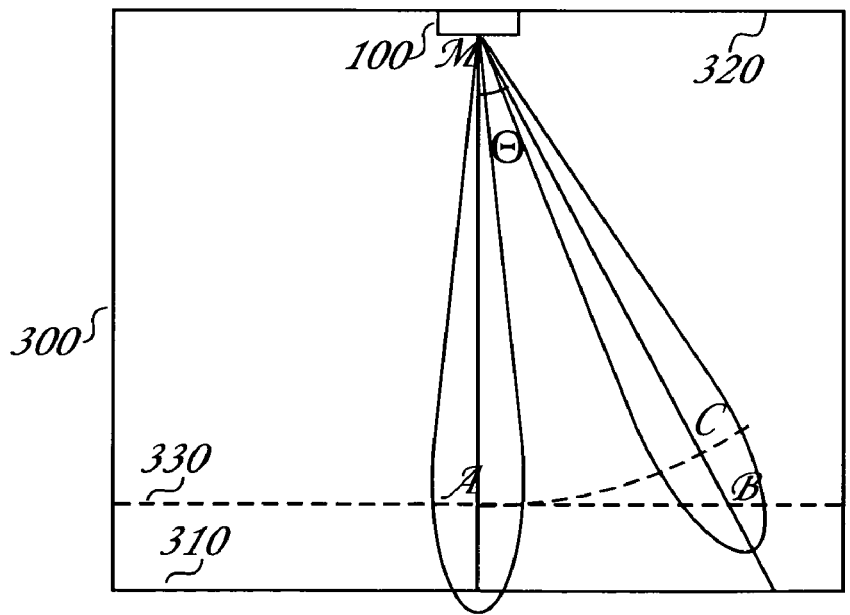
FIG. 2 illustrates how a narrow beam steerable antenna helps to overcome the ambiguity of FIG. 1.

FIG. 2 illustrates a scenario of FIG. 1 where the radar 100 mounted on the ceiling 320 in a room 300 utilizes a narrow beam antenna that can sweep the monitored volume of interest. Sweeping methods, such as, but not limited to, mechanical sweeping and electronic phase array steering are apparent to those skilled in the art and may be embodied in practice in the present invention.

Referring to FIG. 2, the vertical beam encounters the fall threshold 330 at point A. Whereas the slanted beam at angle $\Theta$ encounters the threshold 330 at point B which differs in distance from the radar 100 by the length of segment BC. The difference in distance from the radar 100 to the threshold plane 330 as a function of angle $\Theta$ which is governed by simple geometrical relationships and are easily expressed, for example, by trigonometric functions. The threshold is consistently adjusted accurately as a function of angle $\Theta$ when processing fall detection.

Figure 3:
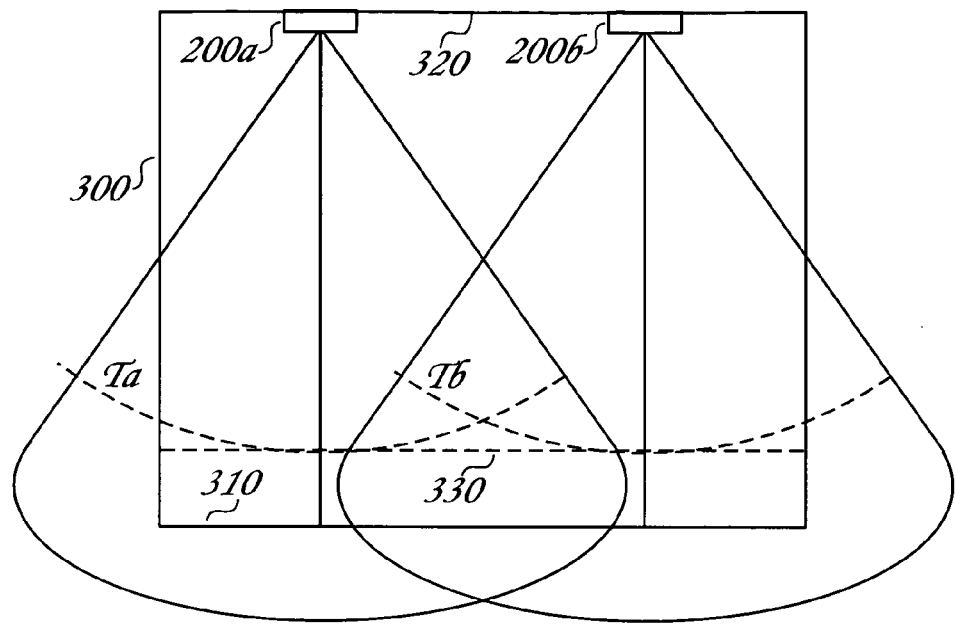
FIG. 3 illustrates an example of a wide beam radar array configured for reducing the ambiguity of FIG. 1.

FIG. 3 illustrates multiple fixed beam radars, such as 200a and 200b, mounted on the ceiling 320 in a manner where the beams partially overlap coverage of the monitored volume. The fixed beams each flood the assigned segment of monitored volume in its entirety and therefore cannot selectively change the threshold distance as a function of angle $\Theta$. As a result, each fixed beam is restricted to a fixed threshold distance marked Ta and Tb for radars 200a and 200b respectively. It is evident from the illustration of Ta and Tb in FIG. 3 that the combined threshold is not as consistent regarding the distance from the floor 310 as the desired threshold plane 330 is.

Figure 4:
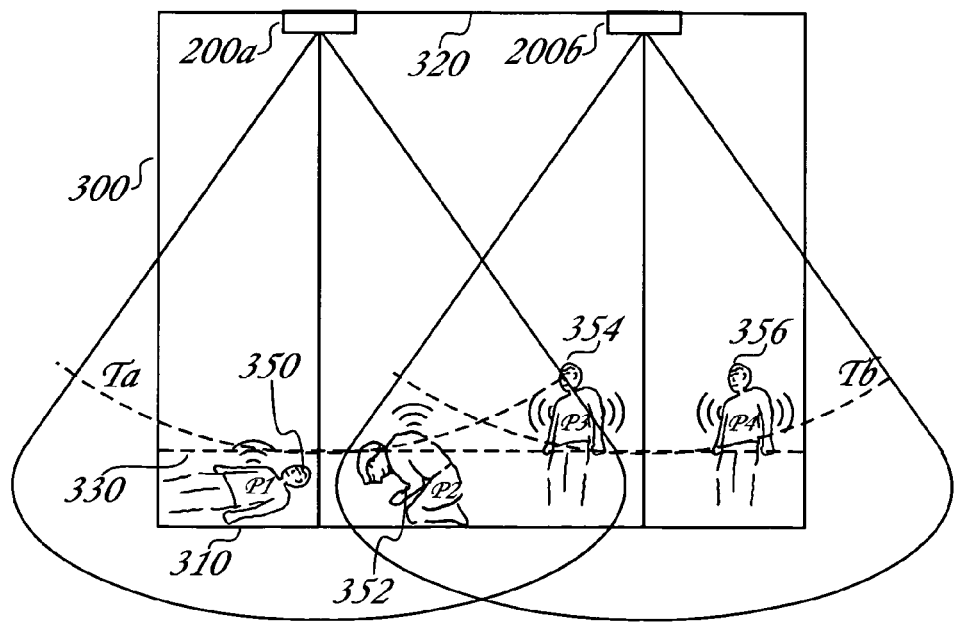
FIG. 4 illustrates an example of fall detection using the array of FIG. 3.

FIG. 4 illustrates the scene of FIG. 3 with the addition of subjects 350, 352, 254, and 356, each shown in different position relative Ta and Tb thresholds. An algorithm for detecting fall condition determines a fall when the radar does not detect the subject's (upper torso) heart/lungs above their respective thresholds while at least one of the radars detects the presence the subject. Following this algorithm, subject 350 is determined to be fallen whereas the other subjects 352, 354, and 356 are not determined as falls.

Figure 5:
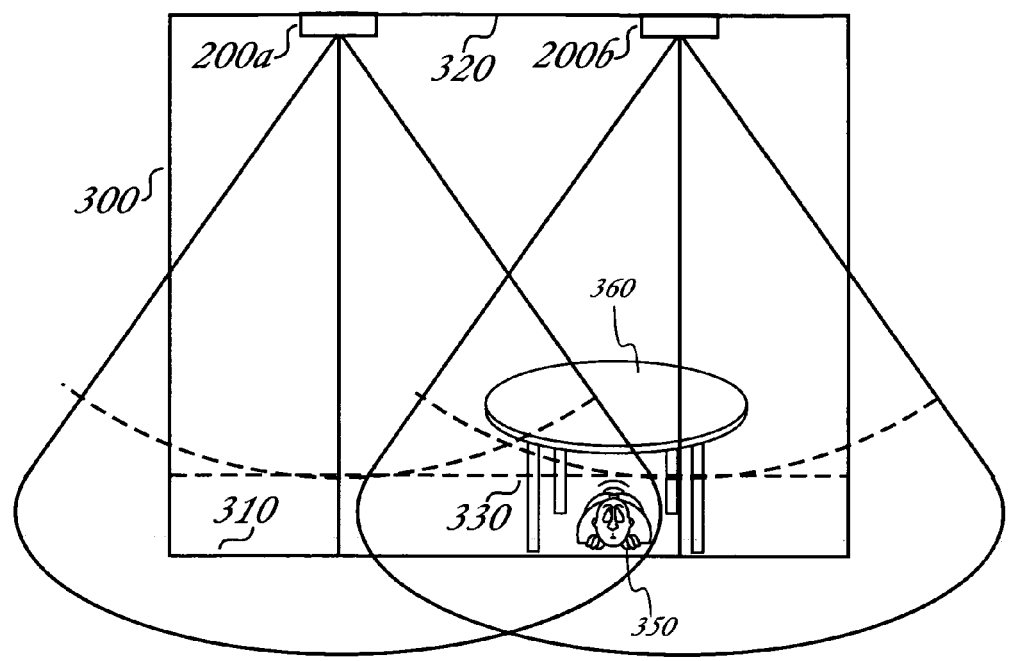
FIG. 5 illustrates radar's visibility through typical furniture in the room.

FIG. 5 illustrates the scene of FIG. 3 with the addition of a table 360 and a subject 350 is shown below the table. This illustration is provided to stress the point that a UWB radar's monitoring power is not obstructed by typical furniture used in homes and institutions.

FIG. 6 illustrates a two-dimensional cross-section of a cluster UWB radar application. The cluster is represented by one transmitter 400 and two receivers 400a and 400b, each at a distance d from the transmitter 400. It is understood that the receiver's and/or transmitter's locations are represented by their respective antennae locations. For example, the receiver antenna and the receiver front-end are collocated whereas the rest of the receiver hardware is collocated with the transmitter. All antennae beams of the receivers and the transmitter cover the proximate volume for monitoring. Delays measured by receiver 400a are T+Ra and by receiver 400b are T+Rb. These two time delay combinations, T+Ra and T+Rb, each represent an ellipse. The general ellipse equation that is symmetrical to the x and y coordinates is:

$$\frac{x^2}{a^2} + \frac{y^2}{b^2} = 1$$

where 2a represents the roundtrip distance corresponding to $T_{Delay}+Ra_{Delay}$ for one ellipse which is also offset by $-d/2$ and where 2a for the second ellipse represents the roundtrip distance corresponding to $T_{Delay}+Rb_{Delay}$ which is also offset by $+d/2$. In addition, each ellipse's focal distance is d. The intersect point of the two ellipses is at the subject's 350 location (upper torso—heart/lungs).

Figure 7:
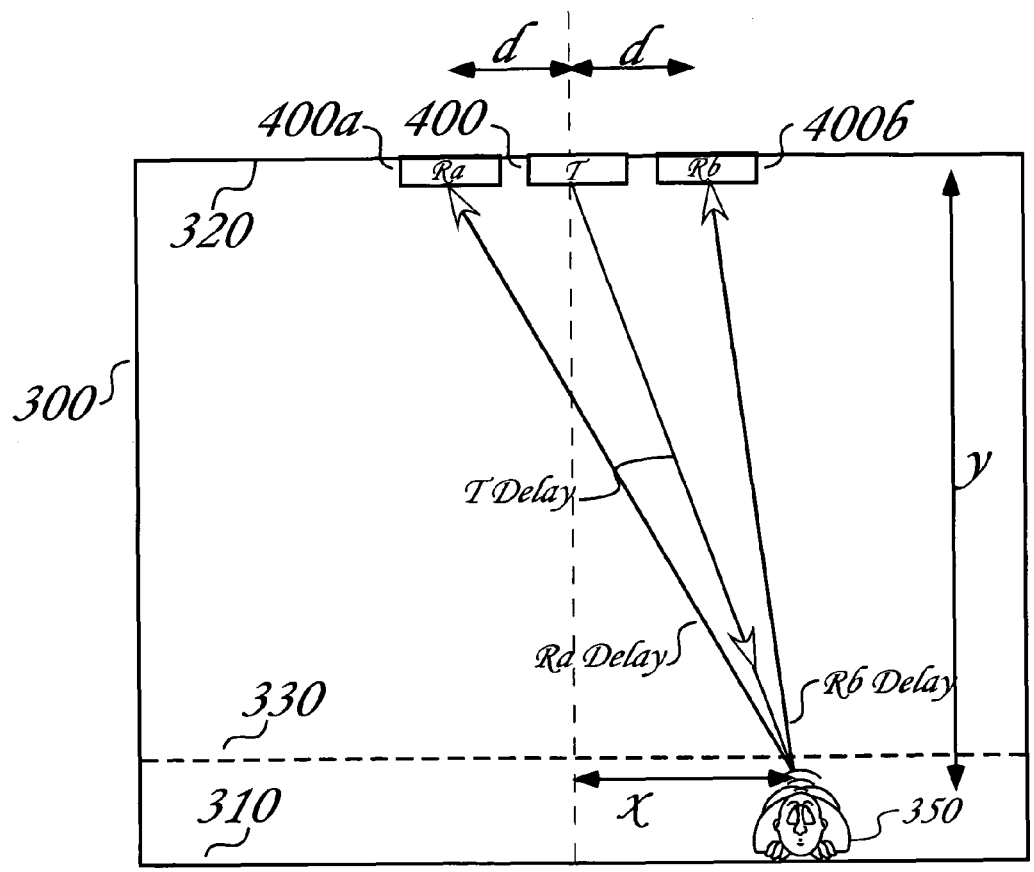
FIG. 7 further illustrates the radar cluster and its ability to detect falls.
Figure 9:
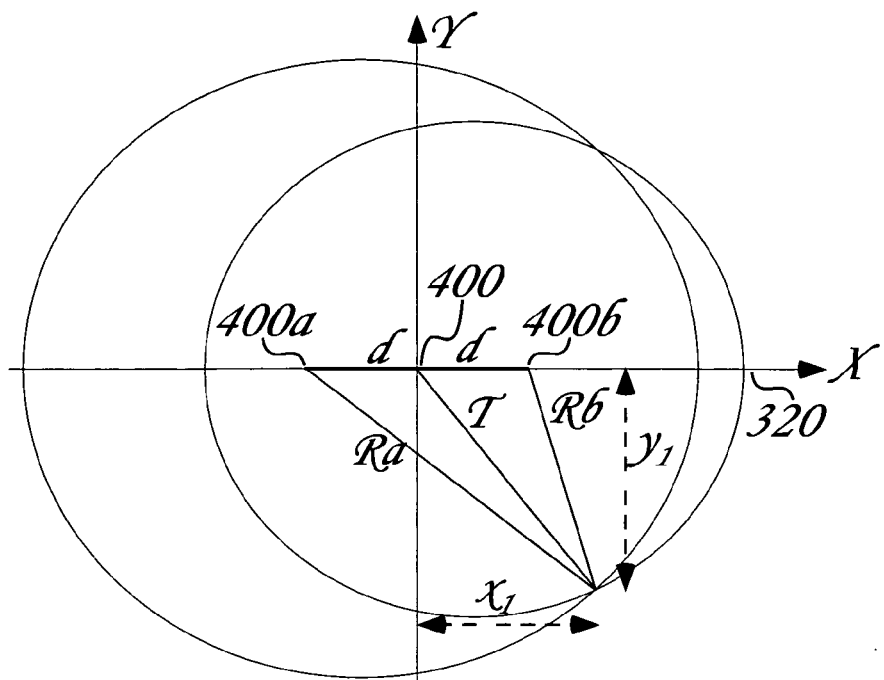
FIG. 9 illustrates the spatial relation between the cluster and the subject's location.

FIG. 7 illustrates the two dimensional cross-section of a cluster UWB radar of FIG. 5 with additional details. The values of x and y at the subject 350 is relative to the cluster transmitter poised at the origin of the coordinates. Note that the illustration of FIG. 7 represents a plane defined by the straight line linking the receivers 400a, 400b, the transmitter T and by the subject's 350 upper torso—heart/lungs. Therefore, y must not be confused with a vertical line i.e., perpendicular to the ceiling. Additional views of the two ellipses and their intersect point are illustrated in FIG. 9.

Figure 8A:
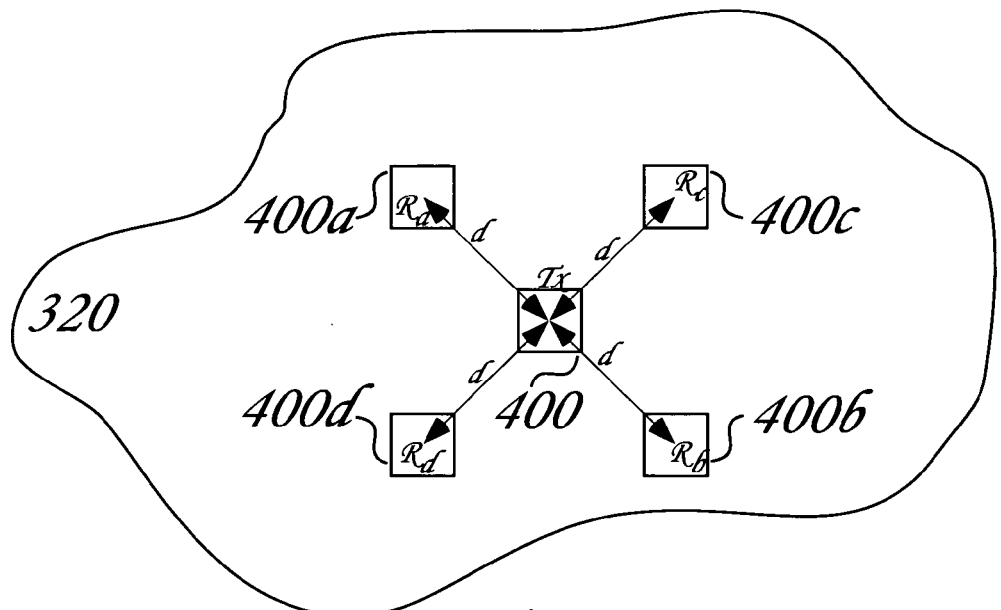
FIG. 8a illustrates a preferred cluster embodiment.

FIG. 8a illustrates a preferred embodiment of the cluster UWB radar. The set of receivers designated 400c and 400d are located on a perpendicular line to the first set of receivers and in line with transmitter 400 and each at a distance d from the transmitter. Execution of the above process using receivers 400c, 400d, and transmitter 400 yield another set of x and y values. This time, the plane of interest is defined by a straight line linking the receivers 400c, 400d, the transmitter T and by the subject's 350 upper torso—heart/lungs. The new plane is perpendicular to the plane defined by receivers 400a, 400b, the transmitter T and by the subject 350.

Figure 8B:
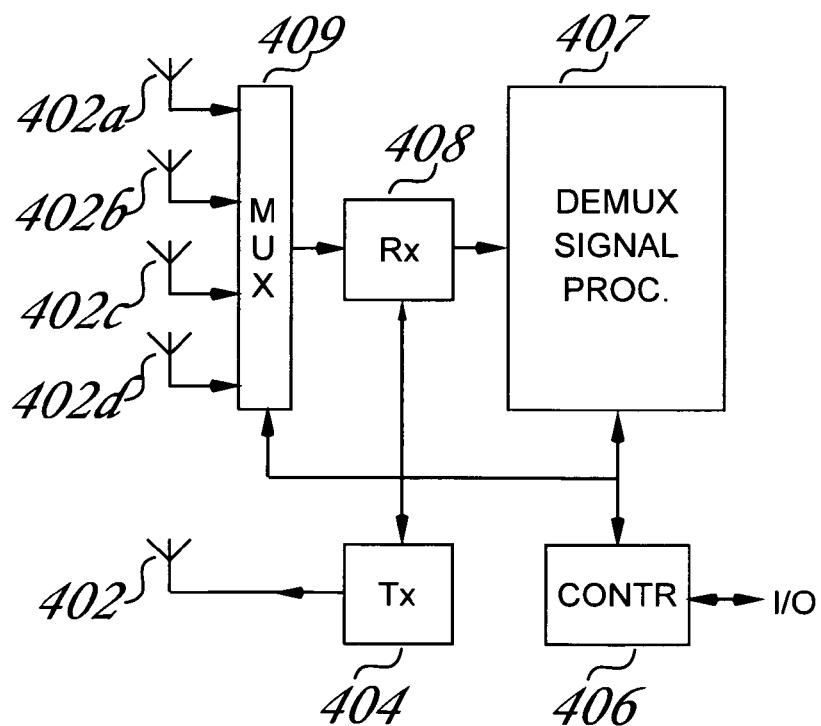
FIG. 8b illustrates a preferred cluster embodiment with multiplexed receiver.

FIG. 8b illustrates another embodiment of a radar cluster block diagram. This radar cluster embodiment's receive antennae 402a, 402b, 402c, and 402d and transmit antenna 402 are spatially diverse as shown in FIG. 8a. However, the signals of the four receive antennae are multiplexed by multiplexer 409 and processed by a single receiver 408. In this example, the multiplexer assigns four time slots, one time slot for each antenna. This implies that each receive antenna's signal is processed every fourth return signal while during the other three return signals, the receiver 408 is occupied with signals of the other antennae; however, the present invention is not limited to this particular multiplexing approach. For example, each time slot could accommodate multiple return signals. Multiplexing does not noticeably diminish the processing results of the compiled Doppler data as long as the return signal repetition rate is higher than the sampling rate required for the Doppler processing. Indeed, the present invention processed Doppler signal i.e. the heartbeat rate and respiration rate are very low and even the fastest body motion falls into a low spectrum when compared to the radar pulse repetition rate. In this example, the output of the receiver 408 is demultiplexed by processor 407 and each of the return signal samples are reconstructed (compiled) according to their respective receive source antennae. Subsequent processing determines the location of the subject's upper torso by methods such as, but not limited to, cross-correlation and trigonometric evaluation. The controller 406 coordinates the overall operation of the radar cluster. The controller 406 and processor 407 also control the housekeeping communications with other radar clusters. The distinction between the controller 406 and processor 407 is for clarity only. The present invention is not limited to this configuration. For example, these functions can all be processed by a single processor or multiple processors without deviating from the scope and spirit of the present invention. FMCW radar is not illustrated in the communication mode, however, multiplexing and/or modulating the FMCW transmitter output for the purpose of communication is equally applicable.

Figure 8C:
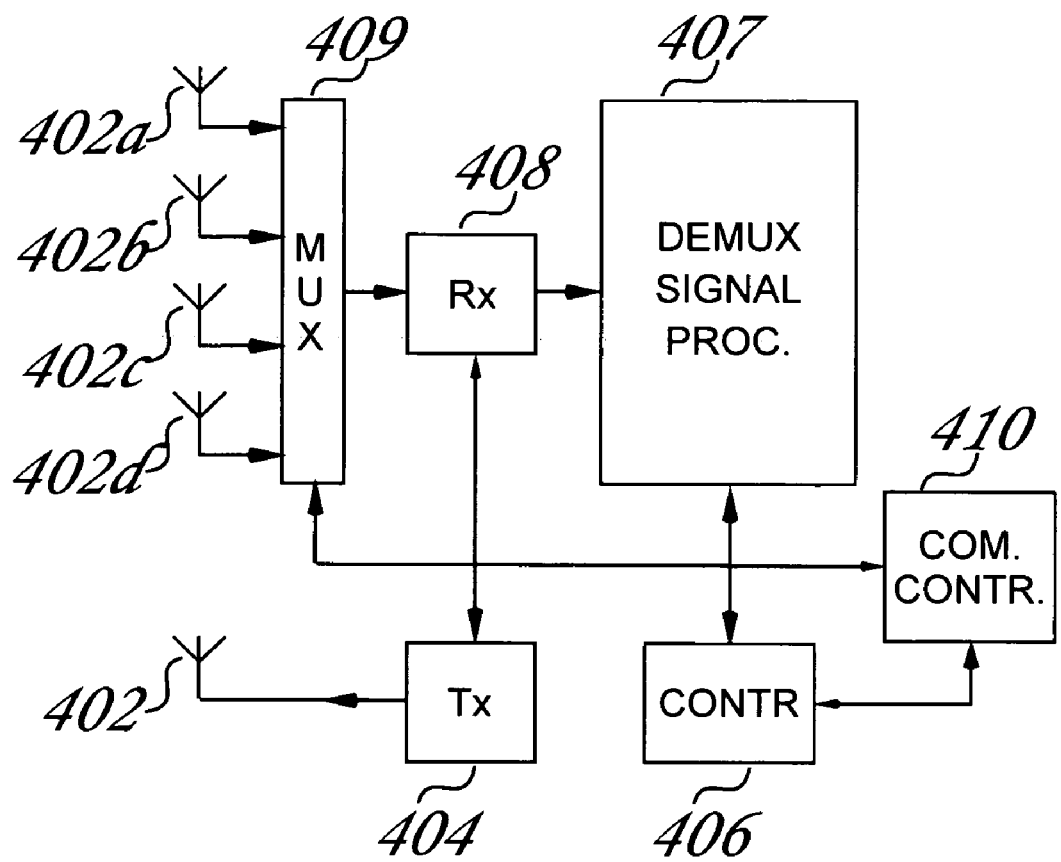
FIG. 8c illustrates a preferred cluster embodiment with multiplexed receiver and integtated comunications.

FIG. 8c illustrates yet another embodiment of present invention with further utility of the radar key component (receiver and transmitter) for housekeeping coordination functions. Although a system using multiple radar clusters, its housekeeping network can be achieved in many forms such as wired and wireless in any ISM or other approved spectrum band. For a wireless network, it seems to be more efficient to choose wireless capabilities of the radar itself FIG. 8c is similar to FIG. 8b but for the added communications controller 410. This addition is presented for functional clarity only. For example, all functions, including communications, can be processed by a single processor or multiple processors without deviating from the scope and/or spirit of the present invention. The communication function is accomplished by modulating the radar pulses or the carrier of FMCW in such a way that they retain radar integrity and provide a mode of communication Another approach that separates the radar functions from the communications function overcomes the limitations of additional complexity or compromise of the radar and/or the communication functions by a change to the multiplexing scheme. The four way radar multiplexing in this case is conducted as in FIG. 8b but in addition, multiplexing time slot(s) are assigned to communications. During the communications time slot, any of the four receive antennae can be used as well as the transmit antenna. It is further possible to use any modulation technique since radar function no longer shares communication time slots. Even the most elementary modulation technique, the ON-OFF Keying (OOK) is perfectly suitable for this application and will not suffer loss of receiver synchronization due to transmission of long strings of zeros because the radar time slots are interleaved with communication time slots by virtue of multiplexing the two functions (radar and communications). Thus, the radar transmission that is always a "one, interrupts long strings of "zeros". The present invention is not limited to any specific multiplexing configuration of timeslot assignment.

The radar cluster receiver receives signals that are initiated at its own transmitter and reflected from the targets. Much of the transmitted energy is absorbed by the environment and only a fraction of it is reflected and received by the receiver. This signal attenuation limits the radar's range of effective operation. However, communication is conducted between two or more clusters using line of sight or deflected signals and will therefore substantially increase the range for communications relative that of the radar. This feature allows cluster spacing in an efficient manner with less radar coverage overlap if so desired.

Figure 10:
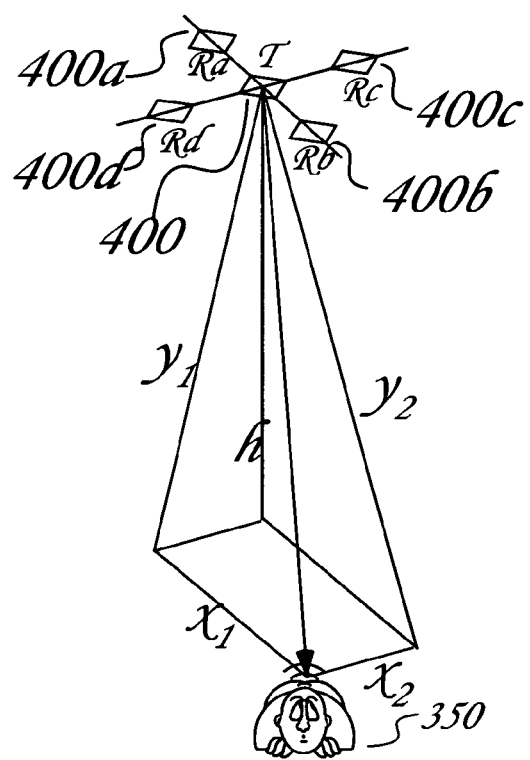
FIG. 10 illustrates an example of the spatial relation between two cluster planes that enable determination of a vertical distance from the cluster to the subject.

FIG. 10 illustrates a combined result h of the cluster UWB radar. The values x and y are now represented by $x_1$ and $y_1$ for the plane defined by receivers 400a, 400b, the transmitter T and by the subject 350 and as $x_2$ and $y_2$ for the plane defined by receivers 400c, 400d, the transmitter T and by the subject 350. Note that h is derived by but not limited to simple trigonometric derivation. For example: h=$y_1$ cos [arcsin ($x_2 \div y_1$)], h=$\sqrt{y_1^2 - x_2^2}$ (Pythagoras), other analytical and or heuristic methods. The true vertical distance h of the subject 350 from the ceiling also provides the subject's proximity to the floor based on the height of the room. It is further understood that the invention is not limited to the described structure of the cluster or to perpendicular planes for derivation of the subject's 350 proximity to the floor. It is noted that the present invention is not limited to the cluster being mounted on the ceiling nor is it restricted in determining proximity to the floor. The present invention encompasses any multidimensional relafionship of a subject to another entity of any spatial complexity.

FIG. 11 illustrates a second preferred embodiment of a vertical 2D cluster comprised of one transmitter T and two receivers Ra and Rb with distance d for space diversity between the antennae 600, 600a, and 600b. The vertical distance h of the transmitter 600 to the subject's upper torso 350 is the dimension of interest and can be derived from round trip delay measurement measured by receiver 600a (T+Ra) and by receiver 600b (T+Rb). These two time delay combinations, T+Ra and T+Rb, each represent an ellipse as a locus. The general ellipse equation that is symmetrical to the h and r coordinates is:

$$\frac{h^2}{a^2} + \frac{r^2}{b^2} = 1$$

where 2a represents a roundtrip distance corresponding to $T_{Delay}+Ra_{Delay}$ for one ellipse which is also offset by $-d/2$ along the vertical h axis and where 2a for the second ellipse represents the roundtrip distance corresponding to $T_{Delay}+Rb_{Delay}$ which is also offset by $+d/2$ along the vertical h axis. In addition, each ellipse's focal distance is d. The intersect point of the two ellipses is at the subject's 350 location (heart/lungs).

The embodiment of FIG. 11 is also suitable for receive antennae multiplexing, in this case two instead of the four antennae as described with regard to FIG. 8. Multiplexing may have dedicated time slots for housekeeping communications or the radar time slots may include modulated radar pulses for data communications. Optional wired or wireless communications at various spectrum bands are within the scope of the present invention.

Figure 12:
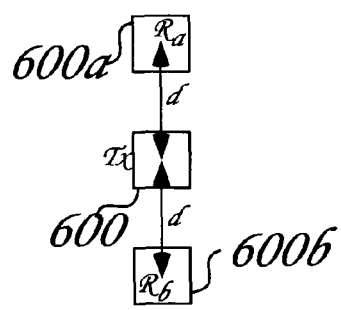
FIG. 12 illustrates another preferred embodiment of (vertical 2D) cluster.

FIG. 12 illustrates an example of vertical 2D cluster that can be mounted on a wall, plugged into a wall power receptacle, placed on the floor as standalone tower, etc.

Figure 13:
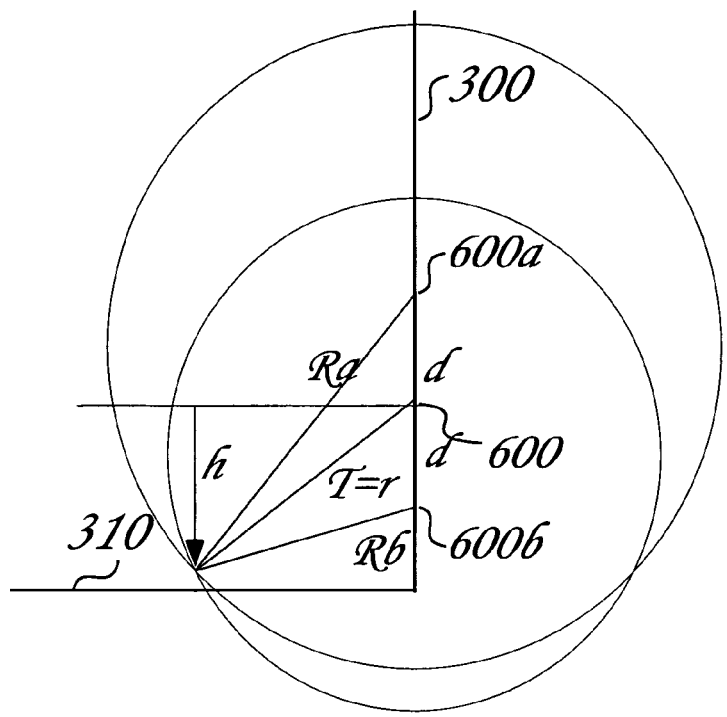
FIG. 13 illustrates the relation between two cluster reflections and the subject.

FIG. 13 shows the relationship of the two above mentioned ellipses and the vertical distance h which is based on the height of the cluster transmitter 600 above ground and determines the position of the upper torso 350 relative the floor.

Figure 14:
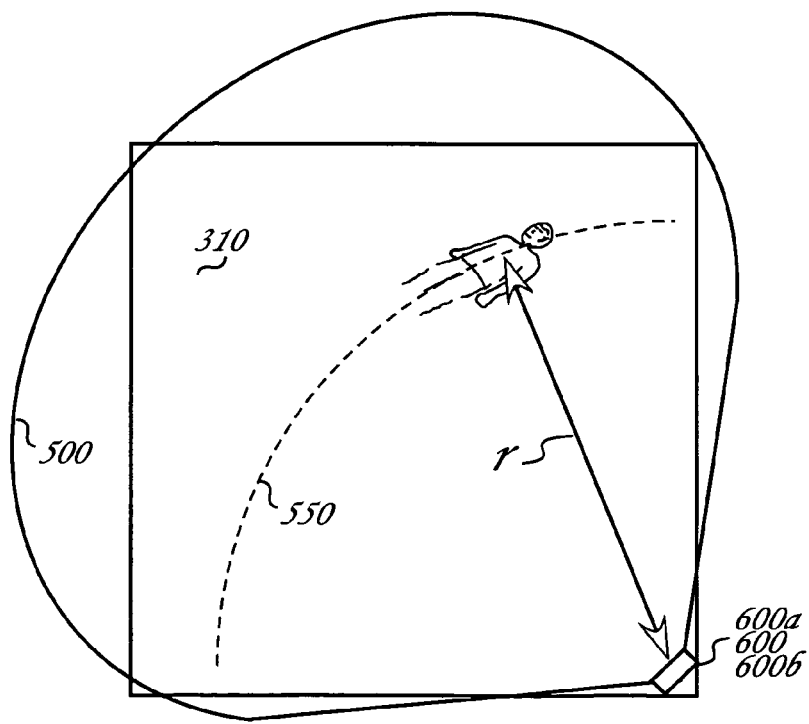
FIG. 14 illustrates a view of the room floor and an example of the locating capability of a subject by the vertical 2D cluster.
Figure 15:
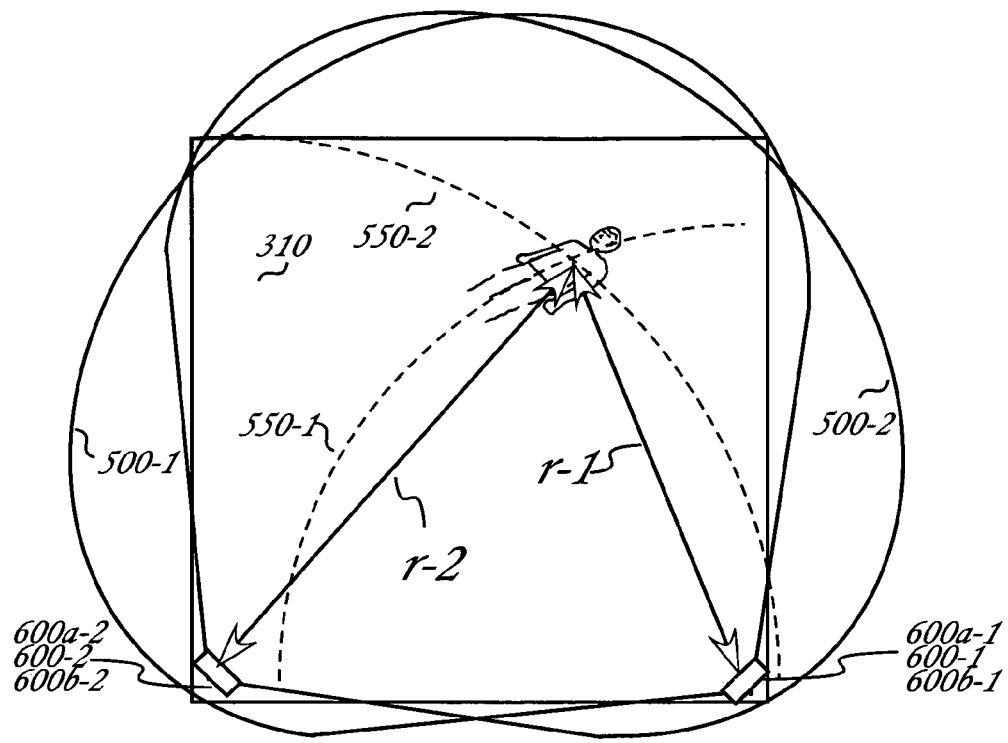
FIG. 15 illustrates a view of the room where two vertical 2D clusters provide the third dimension—azimuth.
Figure 16:
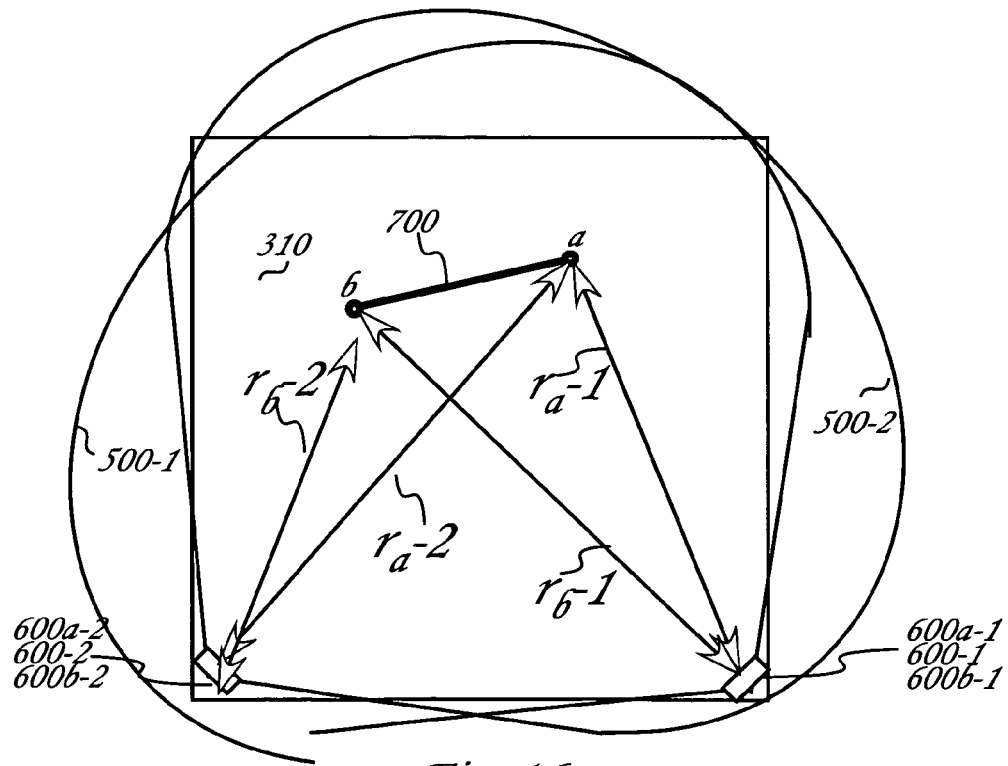
FIG. 16 illustrates the calibration of the premises and the cluster relative location.

FIG. 14 illustrates a vertical view down onto the floor. The value of r is the horizontal distance of the subject's upper torso 350 from the cluster. Note that no azimuth coordinate is obtained by a single cluster and the subject's upper torso 350 could be anywhere on the dotted section 550. However, the main objective of determining h (see FIG. 13) has been achieved. FIG. 15 illustrates the coverage of the same space by at least two radar clusters positioned in a manner that covers the entire space and therefore provides detection redundancy. FIG. 16 illustrates how a dual (a and b) calibrator 700 of known length (distance between a and b) can determine the distance between the two clusters 600-1 and 600-2 by solving the two triangles (triangle one: $r_a$-1, $r_b$-1, and the calibrator and triangle two: $r_a$-2, $r_b$-2, and the calibrator) each defined by three sides. Subsequent solution of triangle defined $r_a$-1, $r_a$-2, and the angle between them provides the distance between the two clusters. Consequently, the multiple radar clusters combined provide the third dimension for locating a subject and can enhance the roaming capability of the vertical cluster.

Figure 17A:
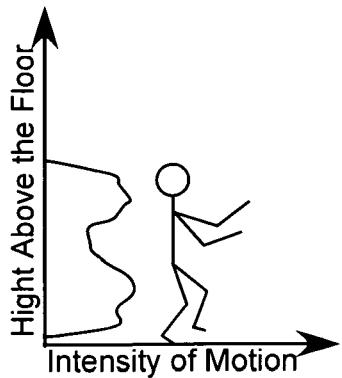
FIGS. 17a and 17b Illustrate motion intensity of a subject as a function of distance from the floor while walking and fallen respectively.
Figure 17B:
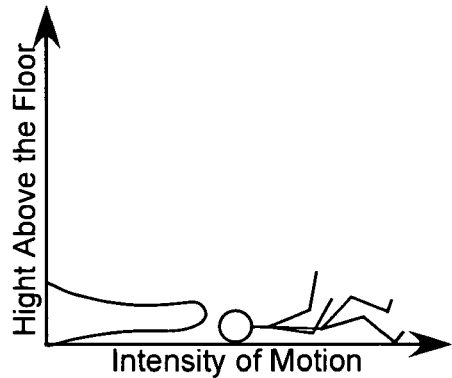

FIGS. 17a and 17b illustrate the processed 2D radar cluster reflection activity signals of a subject's motion while walking and while on the floor struggling to get up respectively. The intensity of said activity/motion is distributed as a continuous function of the distance from the floor. The said activity signals are also an indication of the presence of a subject in response to any combination of rhythmic and random (that are not rhythmic—such as heartbeat or respiration rate) movements of the subject. Consequently, the intensity of said activity signals as a continuous function of their distance from the floor provides an additional criterion for determining whether or not a fall has occurred. The location of the subject, in this case of 2D cluster, is available as a distance from the cluster without azimuth information—this was also discussed and demonstrated previously.

The analysis of the random movements (that are not rhythmic) of the subject that are restricted to those fall within the spectrum of human activity. The analysis can be further refined by customization of the spectral pattern (signature) of the activity/motion of the subject. This signature is derived after the cluster is installed by adjustment to activity signature of a subject as learned from data acquired over time.

Figure 18A:
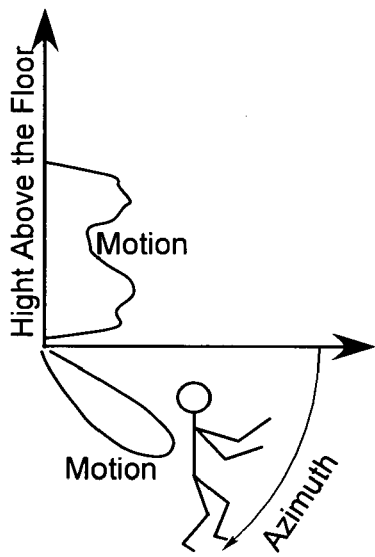
FIGS. 18a and 18b Illustrate motion intensity of a subject as a function of distance from the floor in 3D while walking and fallen respectively.
Figure 18B:
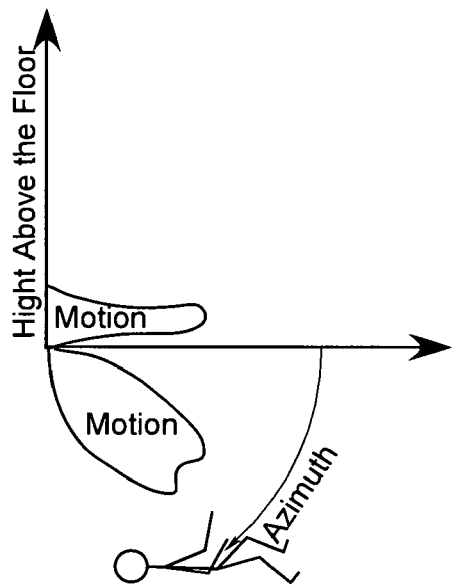

FIGS. 18a and 18b illustrate the processed 3D radar cluster reflection activity signals of a subject's motion while walking and while on the floor struggling to get up respectively. The intensity of said activity/motion is distributed as a continuous function of the distance from the floor—shown on the vertical axis. Because the cluster obtains 3D data, the activity is also distributed on the horizontal plane—shown in the form of polar coordinates. Therefore, the 3D cluster detects subject's presence and the location of a subject by analysis of random movements of the subject and their intensity as a continuous function of their distance from the antennae cluster and azimuth. Consequently the subject can be tracked within the monitored area in addition to fall detection when it occurs.

It is understood and is within the scope and spirit of the present invention that the radar units may additionally or alternately detect the presence and location of a subject by analysis of random movements without considering the rhythmic body motions of the subject and their intensity as a continuous function of their distance from the antennae cluster and azimuth in addition to the distribution of their intensity as a continuous function of their distance from the floor.

All radar cluster embodiments can analyze the reflected return signals of targets other than the subject, filter them and block them out. The criteria for disregarding signals that are not related to subject's activity are defined by their spectral signatures, such as but not limited to, vibration of appliances and other signals outside the range of the human activity spectrum.

It is noted that the present invention is not limited to the algorithmic derivation of h using the principles of geometry, trigonometry, vector analysis, etc. as shown in the examples above. Alternate approaches are equally within the scope and spirit of the invention. Both algorithmic and heuristic method applications, such as, but not limited to, statistical moments, extrapolation from empirical calibration data, adapting to changing environment, etc., are equally applicable in the present invention.

Further, it is understood that the placement (or placements) of subjects captured by the UWB radar can be processed substantially "in real time" (e.g., at the time of capturing the data), or stored in, for example, a memory, for processing at a later time and/or at a location remote from the cluster, without departing from the spirit and/or scope of the invention.

In the present invention, a database is employed to maintain a record of calibration data collected as part of the manufacturing process and/or post installation calibration data. This data base, although optional, is likely to enhance the accuracy of the fall detection process. The post installation calibration provides data enabling the construction of virtual mapping of the monitored premises.

In the present invention, fall detectors with augmentations, such as, but not limited to, audio, for example, indicate that a fall condition has been detected and that alarm to summon help is about to be initiated. This warning is an alert that allows the subject to reset the alert condition in case of a false alarm. The reset of the alarm can be accomplished, for example, by pushing a button, speech recognition, etc. In the case of residential users, the alarm may be conveyed to an emergency response service, or other parties using, for example, an autodial telephone communications system used for fire alarm, intrusion alarm, etc.

It is noted that the subject may be monitored by an entity, such as, but not limited to, for example, an emergency response center that is located at a site remote from the location of the subject. In such a situation, a two-way voice communications system is incorporated into the monitoring system, so that the monitoring personnel can communicate with the subject to determine whether the alarm is genuine. In the present invention, the two-way communications system operates without any user (subject) intervention (i.e., need to pick up a telephone, press a switch on a call pendant, etc.) when the alarm is activated. However, other types of communications systems may be used without departing from the spirit and/or scope of the invention. These features are effective for optimizing caregiver's resources, particularly in the case of assisted living facilities and community dwellers.

A cluster or a group of clusters require the capability for interfacing to an alarm condition conveyance link or network. Such an interface device must be able to communicate, directly or indirectly, with all the clusters related to a given monitoring system since each of the clusters could be the one initiating an alarm call after a fall has been detected. The interface device (not shown) communications with the clusters is most conveniently facilitated by the same network that facilitates the housekeeping communications between clusters which has already been described in this specification. When the communications between clusters employs the same spectrum and many of the same components as the radar, the interface device will facilitate its own communications components compatible with the radar cluster's network. The interface device can alternately be physically connected to one of the clusters and use the cluster's housekeeping communication facility with the rest of the clusters. Optionally, housekeeping communications also convey audio to facilitate a dialog between the emergency response facility and the monitored individual or one-way instructions for the individual. Although one interface device per system has been described, multiple interface devices are within the scope of present invention. Multiple interface devices will eliminate a single point of failure and increase system reliability.

Video surveillance of the monitored premises in conjunction with the UWB cluster monitoring provides an additional confirmation tool of false or real alarms. For privacy reasons the video surveillance may be, but is not limited to, for example, access controlled and/or turned on only when the UWB cluster monitoring detects a fall, etc.

Voice analysis for stress or other distress cues and voice recognition in conjunction with the UWB cluster monitoring can provide additional clues that an alarm condition exists. The algorithm for allocating the link between voice analysis, voice recognition for calls of distress, and the UWB cluster monitoring is of wide spectrum: from total independence to tightly linked.

The radar fall monitoring system optionally tracks the subject throughout the monitored space, such as, but not limited to, a house. Tracking of the monitored individual is further enhanced when in conjunction with the virtual mapping. The determination that the individual left the premises and or returned to the premises using the designated egress and ingress respectively can be determined by correlating with the virtual map of the premises. The loss of upper torso/chest cavity signal can be reconciled as a result of the individual exiting the premises as opposed to loss of the signal due to a medical reason or system failure, such as, having heart beat and or breathing difficulties. In addition, such a virtual map reduces the processing power by restricting it to the clusters monitoring the subject and the immediately adjacent clusters.

The radar fall monitor's tracking capability also provides an optional record of subject's daily activities which is kept in a database for reference. When behavior outside the ordinary occurs, an alert condition may be processed. Typically, distributed motion detection sensors are employed for this purpose by others. However, the motion sensors register only a transitory condition of a subject whereas the present invention tracks the subject continuously whether in motion or not and determines the subject location at all times.

DSP, such as, but not limited to, fast Fourier transforms (FFT) can be applied for distinguishing between a presence of a single subject from among additional subjects because heart beat and/or breathing lungs are unlikely to be synchronized in two individuals. These rate and/or phase differences are visible in DSP analysis, for example, in the frequency domain (spectral representation of the signal). In the case of pets, the heart rate is typically much higher than that of humans so that pets and humans are easily distinguished from each other. Cats typically have heart rates between 160 to 220 beats per minute. Normal respiratory rate in a cat is 20 to 30 breaths per minute. A dogs' heart rate is 180 beats a minute for puppies and 60-160 beats per minute for most adult dogs (180 beats a minute for toy breeds with respiration at 10 to 30 breaths per minute). System performance optimization for a person living alone, a couple living together, pets on the premises, etc., is provided in a setup menu.

Optionally, a caregiver entering the scene can automatically disable the alarm, for example, by wearing a mechanically oscillating/vibrating device or a wireless device that is recognized by the system as unique to a caregiver. The mechanically oscillating device, such as, but not limited to, piezoelectric, motorized, etc., vibrates at a distinct frequency which is in a different spectrum than the heartbeat or lung motion, such as, for example, low ultrasound. Since the vibration frequency can be controlled, an additional radar Doppler processing filter can be tuned to detect the vibration concurrently with the fall detection tasks while using the same basic hardware. When the vibration is detected, it is interpreted as a caregiver tag i.e., a caregiver is present. It is noted that alarm disabling can be accomplished by means other than wireless device and are in the scope of present invention. This feature is particularly effective in nursing homes where supervised activities are not subject to alarm.

Similar vibrating tags vibrating at different frequencies may each be used as a marker for the radar, such as, but not limited to, a calibration device, delimiter of specific physical boundary, etc. For example, a vibrating marker can be placed in a strategic location on a bed for determining that the subject is in bed (and his relative location to the bed) or that he is exiting the bed. A bed, wheelchair, chair, etc., exit monitor can therefore be incorporated into the radar fall detector at marginal cost.

In the disclosed invention, the notification of an alarm is conveyed via a telephone line, internet connectivity or other communications that is interfaced to an external alarm system (not shown) to provide an indication, such as, but not limited to, an audible alarm, to the attending personnel. It is noted that the present invention may interface to an existing nurse-call system provided in, for example, many assisted living institutions. Further, while the present invention discloses an audible alarm, it is understood that a non-audible alarm, such as, but not limited to, for example, a visual indicator, may be employed either in place of or in addition to the audible alarm without departing from the spirit and/or scope of the invention.

Further, the present invention optionally provides for the escalation of the alarm if the attending personnel fails to respond to the initial alarm within a prescribed time period (such as, but not limited to, for example, 5 minutes). For example, when an initial alarm is issued, a higher level alarm (which may be, but is not limited to, for example, alerting the supervisor of the staff and/or placing a call to 911 for emergency help) may be issued if the staff fails to acknowledge that he/she attended to the initial alarm condition within the prescribed time period.

The invention claimed is:

1. A radar system for determining the presence of a subject, comprising:
   a radio wave radar transmitter having one of a fixed antenna and a steerable antenna for transmitting radar signals penetrable through obstructions;
   a radio wave radar receiver having one of a fixed antenna and a steerable antenna for receiving radar signals penetrable through obstructions;
   a signal processor that analyzes random movements of a subject and the intensity of said random movements as a continuous function of the distance from a floor; and
   wherein the signal processor determines a vertical profile of the intensity of said random movements and based on said vertical profile further determines the presence of a subject based on the location of their upper torso.

2. The radar system of claim 1, wherein the radar signals comprise at least one of Ultra Wideband, Spread Spectrum and modulated wave formats.

3. The radar system of claim 2, further comprising a radar cluster containing one radar transmitter and multiple radar receivers, such that at least a two dimensional location of the subject is resolved.

4. The detector system of claim 2, wherein the signal processor determines the distance of the subject from the floor based on an analysis of the distribution of intensity of said random movements along a vertical axis relative to the floor.

5. The radar system of claim 2, wherein the determination of the distance of the subject from the floor is further determined by analysis of the spectral pattern over time of the activity/motion of the subject as determined by observing over time the vertical profile of the intensity of said random movements.

6. The radar system of claim 2, wherein the signal processor provides an alert via a communications link.

7. The radar system of claim 2, further comprising a receiver programmable signal gating, such that the distance over which the signal processor performs its analysis is limited to a desired maximum distance from the transmit and receive radar antennae.

8. The radar system of claim 4, where at least two receiver antennae are displaced in a proximate vertical orientation.

9. The radar system of claim 4, where at least one antenna is multiplexed such that operations to determine the height of the subject from the floor occur during some time periods and other time periods are utilized for housekeeping or alert related operations.

10. The radar system of claim 9, where said at least one antenna of a first radar system communicates with at least one antenna of a second radar system during said time periods utilized for housekeeping or alert related operations.

11. A radio wave radar system, comprising:
    a single radio wave radar unit for monitoring a volume within a premises, wherein radio waves emitted by at least one radio wave transmitter contained within said unit and received by at least one radio wave receiver contained within said unit are penetrable through obstructions;
    a communications link between said radio wave radar system and an emergency responder;
    a signal processor that analyzes random movements of the subject and the intensity of said random movements as a continuous function of the distance from a floor;
    wherein the signal processor determines a vertical profile of the intensity of said random movements and based on said vertical profile further determines the distance of the subject's upper torso relative to the floor; and
    wherein an alert is transmitted to the emergency responder when the radio wave radar system has determined that a subject whose upper torso is a specific distance from the floor is within the monitored volume based on detected motion of their upper torso.

12. The radio wave radar system of claim 11, wherein at least one transmitter and at least one receiver are multiplexed in order to implement said communications link between said radio wave radar g system and an emergency responder during time periods when said transmitter and receiver are not used for monitoring said volume, within said premises.

13. A radar system for detecting the presence of a subject's upper torso within a monitored premises, comprising:
    a radio wave radar transmitter having one of a fixed antenna and a steerable antenna for transmitting radar signals penetrable through obstructions;

a radio wave radar receiver having one of a fixed antenna and a steerable antenna for receiving radar signals penetrable through obstructions in order to monitor a subject within the premises, and comprising at least one of Ultra Wideband, Spread Spectrum and modulated wave formats; and a signal processor that analyzes random movements of the subject and the intensity of said random movements as a continuous function of the distance from a floor, wherein the signal processor determines a vertical profile of the intensity of said random movements over time and based on said vertical profile further determines the presence of a subject within the monitored premises based on determined activity of the subject's upper torso.

14. The radar system of claim 13 wherein said transmitter and receiver are multiplexed in order to implement a communications link between said radar system and an emergency responder during time periods when said transmitter and receiver are not used for monitoring said subject within the premises.

\* \* \* \* \*